United States Patent [19]

Slavin

[11] Patent Number: 5,989,574

[45] Date of Patent: Nov. 23, 1999

[54] WEIGHT LOSS COMPOUND AND METHOD OF USING

[76] Inventor: Andrew B. Slavin, 349 Eagle Dr., Jupiter, Fla. 33477

[21] Appl. No.: 09/056,481

[22] Filed: Apr. 7, 1998

Related U.S. Application Data

[63] Continuation-in-part of application No. 08/713,763, Sep. 13, 1996, and application No. 09/027,647, Feb. 23, 1998.

[51] Int. Cl.$^6$ .............................. A61K 6/00; A61K 7/00; A61K 33/34; A01N 59/20

[52] U.S. Cl. ......................... 424/401; 424/441; 424/630; 424/641

[58] Field of Search .............................. 426/72; 424/401, 424/441, 630

[56] References Cited

U.S. PATENT DOCUMENTS

| | | |
|---|---|---|
| 4,144,357 | 3/1979 | Mohammed .............................. 426/96 |
| 4,393,049 | 7/1983 | Horrobin . |
| 4,784,861 | 11/1988 | Gori . |
| 5,215,750 | 6/1993 | Keane, II . |

OTHER PUBLICATIONS

"Losing Weight Safely", Marilynn Larkin, *FDA Consumer Magazine,* Jan.–Feb. 1996, FDA Home Page excerpt, pp. 1–4.

"The Facts about Weight Loss Products and Programs", Presented as a Public Service by: Federal Trade Commission, Food and Drug Administration, National Association of Attorneys General, FDA/CFSAN Excerpt from *U.S. Food and Drug Administration FDA/FTC/NAAG Brochure:* 1992, pp. 1–4.

"Treatment of Wilson's Disease with zinc. XIII: Therapy with zinc in presymptomatic patients from the time of diagnosis", GJ Brewer, RD Dick, V Ysbasiayan–Gurkan, V Johnson, Y Wang, Dept. of Human Genetics, University of Michigan Medical School, Ann Arbor, MI 48103, Medline Record excerpt from *Journal of Laboratory and Clinical Medicine,* Jun. 1994, vol. 123 @ pp. 849–858, pp. 1–2.

"Wilson Disease", GJ Brewer, V Yusbasiyan–Gurkan, Dept. of Human Genetics, University of Michigan Medical School, Ann Arbor, MI 48103, *Medicine,* 1993, vol. 71, No. 3, pp. 139–164.

Interactions of zinc and molybdenum with copper in therapy of Wilson's Disease, GJ Brewer, Dept. of Human Genetics, University of Michigan Medical School, Ann Arbor, MI 48103, Medline Record excerpt from Nutrition, Jan.–Feb. 1995, vol. 11 @pp. 114–116, p. 1.

*Primary Examiner*—Thurman K. Page
*Assistant Examiner*—Sharon Howard
*Attorney, Agent, or Firm*—Allen, Dyer, Doppelt, Milbrath & Gilchrist, P.A.

[57] ABSTRACT

A composition efficacious in aiding weight loss in humans includes a weight-reducing dosage of zinc acetate packaged together with a copper-depletion-preventing dosage of copper gluconate. The zinc acetate is present as essentially the sole active ingredient. The method of using the composition preferably includes administering the zinc acetate and copper gluconate three times per day. In an alternate embodiment, the composition may be administered twice per day. In addition, it has been found that the composition's efficacy is maximized by also imposing a low-fat dietary regime.

14 Claims, No Drawings

WEIGHT LOSS COMPOUND AND METHOD OF USING

BACKGROUND OF THE INVENTION

CROSS-REFERENCE TO RELATED APPLICATION

This application is a continuation-in-part of and claims priority from parent application Ser. No. 08/713,763, "Weight Loss Compound," filed Sept. 13, 1996, and is further a continuation-in-part of and claims priority from application Ser. No. 09/027,647, "Weight Loss Compound and Method of Using," filed Feb. 23, 1998.

FIELD OF THE INVENTION

The present invention relates to compositions efficacious in aiding weight loss and, more particularly, to such compositions for use by humans.

DESCRIPTION OF RELATED ART

In 1992 it was estimated that 50 million Americans would begin a diet. In a survey sponsored by the U.S. Food and Drug Agency and the National Heart, Lung, and Blood Institute of the National Institutes of Health (1991/1992), 5% of women and 2% of men attempted to lose weight with the use of diet pills. Those products considered by the FDA to be over-the-counter weight control drugs are primarily those containing the active ingredient phenylpropanolamine (PPA).

Although current wisdom has indicated that a persistent course of exercise and healthy eating habits is the most likely to succeed, Americans spend an estimated $30 billion a year on diet programs and products. Among such products, for which there is little or no evidence of efficacy, are diet patches (now banned by the FDA), "fat blockers," "starch blockers," "magnet" diet pills to "flush fat out of the body," glucomannan, fillers such as fiber-based products, and *spirulina* (a species of blue-green algae) (Source: U.S. FDA Brochure, "The Facts about Weight Loss Products and Programs," 1992).

Horrobin (U.S. Pat. No. 4,393,049) has disclosed the use of γ-linolenic acid and dihomo-γ-linolenic acid, alone and in combination with zinc, β-lactam antibiotics, or other materials that influence prostaglandin imbalance to treat obesity. The zinc is believed to stimulate the biosynthesis of 1-series prostaglandins.

Gori (U.S. Pat. No. 4,784,861) discloses a preparation for controlling weight that includes fiber-containing materials and water-absorbant substances to form bulk and for providing a coating. In order to replace minerals carried out of the system by the fiber, minteral supplements are also provided, including zinc and copper.

Keane (U.S. Pat. No. 5,215,750) discloses the use of zinc gluconate for inclusion with an L-glutamine-based composition for weight loss or control.

The use of zinc acetate, an anticopper agent, has been utilized for the treatment of Wilson disease, a relatively rare disorder resulting in copper toxicity (see, for example, G. J. Brewer and V. Yuzbasiyan-Gurkan, "Wilson Disease," *Medicine* 71(3), 139–64, 1992). The recommended dosage is 50 mg three times per day. In monitoring patients it was found that serum amylase and lipase levels were mildly elevated during the early months of zinc therapy, which may be due to an increase in induction of the enzymes.

SUMMARY OF THE INVENTION

It is therefore an object of the present invention to provide a composition and method for aiding weight loss in a human.

This object is achieved by the composition of the present invention, which comprises a weight-reducing effective amount of zinc acetate. The zinc acetate is present as the sole active ingredient in the weight-loss process. The composition further comprises a depletion-preventing dosage of copper, preferably present in the form of copper gluconate.

The method comprises the steps of providing a composition comprising a weight-reducing effective dosage of zinc acetate and a depletion-preventing dosage of copper, and administering the composition two or three times per day. Again, the zinc acetate is present as the sole active ingredient in the weight-loss process.

The features that characterize the invention, both as to organization and method of operation, together with further objects and advantages thereof, will be better understood from the following description.

DETAILED DESCRIPTION OF THE PREFERRED EMBODIMENTS

A description of the preferred embodiments of the present invention will now be presented.

A preferred embodiment of the composition of the present invention comprises approximately 40–60 mg, and preferably 50 mg, of zinc acetate packaged with approximately 0.7–2 mg, and preferably 1.3 mg, of copper gluconate, for preventing a depletion of copper in the body. The package is for administering thrice per day, An alternate embodiment of the composition comprises approximately 60–90 mg, and preferably 75 mg, of zinc acetate for administering 2 times per day and approximately 1–3 mg, and preferably 2 mg, of copper gluconate for administering twice per day.

A preferred embodiment of the method of the present invention comprises the step of administering a composition as outlined above of approximately 40–60, preferably 50, mg of zinc acetate packaged with 0.7–2, preferably 1.3, mg of copper gluconate three times per day.

An alternate embodiment of the method comprises the step of administering a composition as outlined above of approximately 60–90, preferably 75, mg of zinc acetate packaged with 1–3, preferably 2, mg of copper gluconate twice per day.

In order to maximize the efficacy of the method, preferably the method further comprises instituting a dietary regime containing dietary fat in a range of 5 to 20 grams of fat per day.

It may be appreciated by one skilled in the art that additional embodiments may be contemplated, including compositions comprising other salts of zinc and copper and administering the composition in other dosages and at different intervals.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the invention described herein are by way of example, and the scope of the invention is not limited to the exact details provided.

Having now described the invention, the composition, the use of preferred embodiments thereof, and the advantageous new and useful results obtained thereby, the new and useful constructions, and reasonable equivalents thereof obvious to those skilled in the art, are set forth in the appended claims.

What is claimed is:

1. A method for effecting weight reduction in a human comprising the steps of:
   providing a composition comprising as essentially a sole active ingredient a weight-reducing effective dosage of zinc acetate and a depletion-preventing dosage of copper; and
   administering the composition three times per day.

2. The method recited in claim 1, wherein the composition comprises zinc acetate in a range of 40–60 mg.

3. The method recited in claim 1, wherein the composition comprises approximately 50 mg of zinc acetate.

4. The method recited in claim 1, wherein copper in the composition is present as copper gluconate.

5. The method recited in claim 1, wherein the composition comprises copper gluconate in a range of 0.7–2 mg.

6. The method recited in claim 1, wherein the composition comprises 1.3 mg of copper gluconate.

7. The method recited in claim 1, further comprising the step of instituting a dietary regime containing dietary fat in a range of 5 to 20 grams per day.

8. A method for effecting weight reduction in a human comprising the steps of:
   providing a composition comprising as essentially a sole active ingredient a weight-reducing effective dosage of zinc acetate and a depletion-preventing dosage of copper; and
   administering the composition twice per day.

9. The method recited in claim 8, wherein the composition comprises zinc acetate in a range of 60–90 mg.

10. The method recited in claim 8, wherein the composition comprises approximately 75 mg of zinc acetate.

11. The method recited in claim 8, wherein copper in the composition is present as copper gluconate.

12. The method recited in claim 8, wherein the composition comprises copper gluconate in a range of 1–3 mg.

13. The method recited in claim 8, wherein the composition comprises 2 mg of copper gluconate.

14. The method recited in claim 8, further comprising the step of instituting a dietary regime containing dietary fat in a range of 5 to 20 grams per day.

* * * * *